United States Patent
Kadyrov

(10) Patent No.: US 9,890,108 B2
(45) Date of Patent: *Feb. 13, 2018

(54) CATALYTIC HYDROGENATION FOR THE PREPARATION OF AMINES FROM AMIDE ACETALS, KETENE N, O-ACETALS OR ESTER IMIDES

(71) Applicant: Renat Kadyrov, Frankfurt (DE)

(72) Inventor: Renat Kadyrov, Frankfurt (DE)

(73) Assignee: Evonik Degussa GmbH, Essen (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/034,135

(22) PCT Filed: Oct. 15, 2014

(86) PCT No.: PCT/EP2014/072109
§ 371 (c)(1),
(2) Date: May 3, 2016

(87) PCT Pub. No.: WO2015/067448
PCT Pub. Date: May 14, 2015

(65) Prior Publication Data
US 2016/0264513 A1   Sep. 15, 2016

(30) Foreign Application Priority Data
Nov. 5, 2013  (EP) ..................................... 13191498

(51) Int. Cl.
| | |
|---|---|
| *C07C 209/52* | (2006.01) |
| *C07B 43/04* | (2006.01) |
| *C07C 209/68* | (2006.01) |
| *C07C 213/00* | (2006.01) |
| *C07C 253/30* | (2006.01) |
| *C07D 295/023* | (2006.01) |
| *C07D 295/027* | (2006.01) |
| *C07D 295/03* | (2006.01) |
| *C07C 213/02* | (2006.01) |

(52) U.S. Cl.
CPC ............ *C07C 209/52* (2013.01); *C07B 43/04* (2013.01); *C07C 209/68* (2013.01); *C07C 213/00* (2013.01); *C07C 213/02* (2013.01); *C07C 253/30* (2013.01); *C07D 295/023* (2013.01); *C07D 295/027* (2013.01); *C07D 295/03* (2013.01); *C07C 2601/14* (2017.05)

(58) Field of Classification Search
None
See application file for complete search history.

(56) References Cited

U.S. PATENT DOCUMENTS

| | | | | |
|---|---|---|---|---|
| 4,141,917 A | * | 2/1979 | Kunstmann | C07D 235/26 548/306.4 |
| 2012/0253042 A1 | | 10/2012 | Milstein et al. | |
| 2016/0272571 A1 | | 9/2016 | Kadyrov | |

FOREIGN PATENT DOCUMENTS

DE   604 277   10/1934

OTHER PUBLICATIONS

English translation of portion of Office Action for Chinese application 201480072289.6 filed Oct. 16, 2014, counterpart for copending U.S. Appl. No. 15/034,120.
Xiao, et al., "A Direct and General Method for the Reductive Alkylation of Tertiary Lactams/Amides: Application to the Step Economical Synthesis of Alkaloid (−)-Morusimic Acid D," *J. Org. Chem.* 78:8305-8311 (Aug. 2013).
English translation of the International Search Report for PCT/EP2014/072109 filed Oct. 15, 2014.
English translation of the Written Opinion of the International Searching Authority for PCT/ EP2014/072109 filed Oct. 15, 2014.
English translation of the International Preliminary Report on Patentability for PCT/EP2014/072109 filed Oct. 15, 2014.
European Search Report with partial machine translation attached for EP 13 19 1498 (related to PCT/EP2014/072109) dated Mar. 13, 2014.
English translation of the International Search Report for PCT/EP2014/072184 (international stage of copending application 15/034,120) filed Oct. 16, 2014.
English translation of the Written Opinion of the International Searching Authority for PCT/EP2014/072184 filed Oct. 16, 2014.
English translation of the International Preliminary Report on Patentability for PCT/EP2014/072184 filed Oct. 16, 2014.
European Search Report with partial machine translation attached for EP 13 19 1503 (related to PCT/EP2014/072184) dated Mar. 13, 2014.
Balaraman, et al., "Direct Hydrogenation of Amides to Alcohols and Amines under Mild Conditions," *J. AM. CHEM. SOC.* 132(47):16756-16758 (Dec. 2010).
Sashida, et al., "Studies on Diazepines. XXIX.[1)] Syntheses of 3H- and 5H-1,4-Benzodiazepines from 3-Azidoquinolines," *Chemical and Pharmaceutical Bulletin, Pharmaceutical Society of Japan* vol. 35:4110-4116 (Jan. 1987).
Stein, et al., "Catalytic Hydrogenation of Amides to Amines under Mild Conditions," *Angew. Chem. Int.* 52(8):2231-2234 (Feb. 2013).
Nishimura, "Handbook of Heterogeneous Catalytic Hydrogenation for Organic Synthesis," pp. 406-411, John Wiley and Sons, Inc., N.Y. (2001).
U.S. Appl. No. 15/034,120, filed May 3, 2016, Kadyrov.
Office Action for U.S. Appl. No. 15/034,120, dated Mar. 22, 2017.
Response to Office Action of Mar. 22, 2017 filed in U.S. Appl. No. 15/034,120 on Jun. 21, 2017.

\* cited by examiner

*Primary Examiner* — Clinton Brooks
(74) *Attorney, Agent, or Firm* — Law Office of: Michael A. Sanzo, LLC

(57) ABSTRACT

The present invention relates to a process for the preparation of amines, comprising the following steps: Reaction of a (i) amide acetal of the general formula (I), or (ii) ketene N,O-acetal of the general formula (II), or (iii) ester imide of the general formula (III) with $H_2$ in the presence of a hydrogenation catalyst, where catalyst and amide acetal or ketene N,O-acetal or ester imide are used in a molar ratio of from 1:10 to 1:100 000 and where a hydrogen pressure of from 0.1 bar to 200 bar is established and where a temperature in the range of from 0° C. to 250° C. is established.

20 Claims, No Drawings

CATALYTIC HYDROGENATION FOR THE PREPARATION OF AMINES FROM AMIDE ACETALS, KETENE N, O-ACETALS OR ESTER IMIDES

CROSS REFERENCE TO RELATED APPLICATIONS

The present application is US national stage of international application PCT/EP2014/072109, which had an international filing date of Oct. 15, 2014, and which was published in German on May 14, 2015. Priority is claimed to European application EP 13191498.8, filed on Nov. 5, 2013. The contents of the priority application is hereby incorporated by reference in its entirety.

The present invention relates to a process for the preparation of amines, where an amide acetal, ketene N,O-acetal or ester imide with $H_2$ in the presence of a hydrogenation catalyst, where catalyst and amide acetal or ketene N,O-acetal or ester imide are used in a molar ratio of from 1:10 to 1:100 000 and where a hydrogen pressure of from 0.1 bar to 200 bar is established and where a temperature in the range of from 0° C. to 250° C. is established. The amide acetals, ketene N,O-acetals or ester imides can be hydrogenated by this process in a highly selective manner and under very mild conditions to give amines.

Reduction of amides is one of the most important methods for the preparation of amines. The classic process is based on the reduction by complex hydrides, although stoichiometric amounts of hydride are required and the selectivity is relatively low. The development of catalytic reduction with hydrogen remains to date one of the greatest challenges. Hydrogenations of this kind are known in the literature, although large amounts (15 mol % and more) of catalyst, very high pressures and temperatures of above 200° C. are necessary in order to achieve useable yields (S. Nishimura, Handbook of Heterogeneous Catalytic Hydrogenation for Organic Synthesis 2001, pp. 406-411, Wiley, N.Y.,). The hydrogenation of tertiary and secondary amides to give amines at 120-160° C. over a bimetallic Pd—Re catalyst has recently been reported (M. Stein, B. Breit, Angew. Chem. 2013, 125, 2287-2290). Despite somewhat milder conditions, a functional group is barely tolerated, even olefinic double bonds and aromatic rings are fully hydrogenated.

By contrast, barely anything is known about the hydrogenolysis of amide acetals and imino ethers. The patent DE 604277C (W. Klempt, F. Brodkorb) describes that the hydrochlorides of the primary imino ethers can be converted with high yields into the primary amines by hydrogenation in the presence of Adams catalyst (platinum oxide). A reworking of experimental protocol 1 from the patent specification has been carried out, and the products were characterized using modern methods (GC-MS and NMR). However, product analysis revealed that, under the conditions stated in DE604277C, for the greatest part bis(dicyclohexylmethyl) amine is formed, a secondary amine with fully hydrogenated benzene rings (Example 1 in the chapter Working Examples).

In the last 50 years the development of synthetic methods for the preparation of amide acetals and imido esters has become a subject of great interest. As is known, the amide acetals and imido esters are nowadays some of the readily accessible substance classes (G. Simchen, Methoden Org. Chem., 1985, E5/1, S. 1-192 (Houben-Weyl); N. Nakajima, M. Ubukata, Science of Synthesis 2005, Vol. 22, pp. 343-360, Thieme Chemistry Stuttgart).

It was therefore the object of the present invention to provide a process for the preparation of amines by means of catalytic hydrogenation of acid amide acetals, ketene N,O-acetals and acid ester imides with hydrogen.

Surprisingly, it has now been found that amide acetals, ketene N,O-acetals and ester imides can be hydrogenated to amines under very mild conditions in the presence of customary hydrogenation catalysts. Here, a very wide variety of functional groups are tolerated; inter alia, nitriles, carboxyl and phosphone groups are retained.

The technical object is achieved by a process for the preparation of amines comprising the following steps:

a. Reaction of an i. amide acetal of the general formula (I),

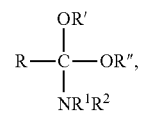

where

R is selected from the group consisting of H, $(C_1-C_{24})$-alkyl, $(C_3-C_{20})$-cycloalkyl, $(C_2-C_{13})$-heterocycloalkyl, $(C_6-C_{14})$-aryl or $(C_3-C_{13})$-heteroaryl, CN, COO—$(C_1-C_{18})$-alkyl, CONH—$(C_1-C_{18})$-alkyl, $CF_3$;

R' and R'' independently of one another are selected from the group $(C_1-C_{24})$-alkyl, $(C_3-C_{20})$-cycloalkyl, $(C_2-C_{13})$-heterocycloalkyl; and $R^1$ and $R^2$ independently of one another are selected from the group consisting of H, $(C_1-C_{24})$-alkyl, $(C_3-C_8)$-cycloalkyl, $(C_2-C_7)$-heterocycloalkyl, $(C_6-C_{14})$-aryl and $(C_3-C_{13})$-heteroaryl;

where also from in each case two radicals selected from R, $R^1$, $R^2$, R' and R'' together, a $(C_2-C_8)$-alkylene bridge can be formed, thus giving a ring with in total 4-11 ring atoms;

or ii. ketene N,O-acetal of the general formula (II)

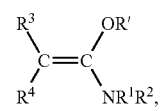

where

R' is selected from the group consisting of $(C_1-C_{24})$-alkyl, $(C_3-C_{20})$-cycloalkyl, $(C_2-C_{13})$-heterocycloalkyl; and $R^1$, $R^2$ independently of one another are selected from the group consisting of H, $(C_1-C_{24})$-alkyl, $(C_3-C_{20})$-cycloalkyl, $(C_2-C_{13})$-heterocycloalkyl, $(C_6-C_{14})$-aryl and $(C_3-C_{13})$-heteroaryl;

$R^3$ and $R^4$ independently of one another are selected from the group consisting of H, $(C_1-C_{24})$-alkyl, $(C_3-C_{20})$-cycloalkyl, $(C_2-C_{13})$-heterocycloalkyl, $(C_6-C_{14})$-aryl and $(C_3-C_{13})$-heteroaryl, CN, COO—$(C_1-C_{18})$-alkyl, CONH—$(C_1-C_{18})$-alkyl and $CF_3$, where also from in each case two radicals selected from $R^1$, $R^2$, $R^3$, $R^4$ and R' together, a $(C_2-C_8)$-alkylene bridge can be formed, thus giving a ring with in total 3-11 ring atoms;

or iii. ester imide of the general formula (III)

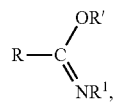

where

R' is selected from the group consisting of $(C_1-C_{24})$-alkyl, $(C_3-C_{20})$-cycloalkyl, $(C_2-C_{13})$-heterocycloalkyl; R is selected from the group consisting of H, $(C_1-C_{24})$-alkyl, $(C_3-C_{20})$-cycloalkyl, $(C_2-C_{13})$-heterocycloalkyl, $(C_6-C_{14})$-aryl or $(C_3-C_{13})$-heteroaryl, CN, COO—$(C_1-C_{18})$-alkyl, CONH—$(C_1-C_{18})$-alkyl, $CF_3$;

$R^1$ is selected from the group consisting of H, $(C_1-C_{24})$-alkyl, $(C_3-C_{20})$-cycloalkyl, $(C_2-C_{13})$-heterocycloalkyl, $(C_6-C_{14})$-aryl or $(C_3-C_{13})$-heteroaryl;

where also from in each case two radicals selected from R, $R^1$ and R' together, a $(C_2-C_8)$-alkylene bridge can be formed, thus giving a ring with in total 4-11 ring atoms;

with $H_2$ in the presence of a hydrogenation catalyst, where catalyst and amide acetal or ketene N,O-acetal or ester imide are used in a molar ratio of from 1:10 to 1:100 000 and where a hydrogen pressure of from 0.1 bar to 200 bar is established and where a temperature in the range of from 0° C. to 250° C. is established.

In the context of the present invention, the term amide acetal refers to all types of amide acetals of the general formula (I), irrespective of whether they are acetals of monoamides or diamides, whether they are cyclic amide acetals or acyclic amide acetals.

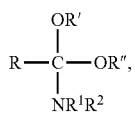

wherein

R is selected from the group consisting of H, $(C_1-C_{24})$-alkyl, $(C_3-C_{20})$-cycloalkyl, $(C_2-C_{13})$-heterocycloalkyl, $(C_6-C_{14})$-aryl or $(C_3-C_{13})$-heteroaryl, CN, COO—$(C_1-C_{18})$-alkyl, CONH—$(C_1-C_{18})$-alkyl, $CF_3$;

R' and R" independently of one another are selected from the group $(C_1-C_{24})$-alkyl, $(C_3-C_{20})$-cycloalkyl, $(C_2-C_{13})$-heterocycloalkyl; and $R^1$ and $R^2$ independently of one another are selected from the group consisting of H, $(C_1-C_{24})$-alkyl, $(C_3-C_8)$-cycloalkyl, $(C_2-C_7)$-heterocycloalkyl, $(C_6-C_{14})$-aryl and $(C_3-C_{13})$-heteroaryl;

where also from in each case two radicals selected from R, $R^1$, $R^2$, R' and R" together, a $(C_2-C_8)$-alkylene bridge can be formed, thus giving a ring with in total 4-11 ring atoms.

R is preferably selected from the group consisting of H, methyl, ethyl, n-propyl, n-butyl, isobutyl, n-pentyl, n-hexyl, cyclohexyl, n-heptyl, n-octyl, phenyl, pyridyl, naphthyl.

R' are R" preferably selected from the group consisting of methyl, ethyl, benzyl, 1,2-ethylene;

$R^1$ and $R^2$ are preferably selected from the group consisting of methyl, ethyl, n-propyl, isopropyl, n-butyl, isobutyl, n-pentyl, n-hexyl, n-heptyl, n-octyl, butanedi-1,4-yl, pentanedi-1,5-yl, hexanedi-1,6-yl and phenyl.

A ring is preferably formed between the radicals R and $R^1$ or $R^1$ and R', where the ring preferably has in total 5, 6 or 7 ring atoms. Preferably formed rings are pyrrolidine, piperidine, morpholine, piperazine, homopiperidine and homopiperazine and derivatives thereof.

In the context of the present invention, the term ketene N,O-acetals refers to compounds of the general formula (II)

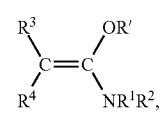

wherein

R' is selected from the group consisting of $(C_1-C_{24})$-alkyl, $(C_3-C_{20})$-cycloalkyl, $(C_2-C_{13})$-heterocycloalkyl; and $R^1$, $R^2$ independently of one another are selected from the group consisting of H, $(C_1-C_{24})$-alkyl, $(C_3-C_{20})$-cycloalkyl, $(C_2-C_{13})$-heterocycloalkyl, $(C_6-C_{14})$-aryl and $(C_3-C_{13})$-heteroaryl;

$R^3$ and $R^4$ independently of one another are selected from the group consisting of H, $(C_1-C_{24})$-alkyl, $(C_3-C_{20})$-cycloalkyl, $(C_2-C_{13})$-heterocycloalkyl, $(C_6-C_{14})$-aryl and $(C_3-C_{13})$-heteroaryl, CN, COO—$(C_1-C_{18})$-alkyl, CONH—$(C_1-C_{18})$-alkyl and $CF_3$, where also from in each case two radicals selected from $R^1$, $R^2$, $R^3$, $R^4$ and R' together, a $(C_2-C_8)$-alkylene bridge can be formed, thus giving a ring with in total 3-11 ring atoms.

R' is preferably selected from the group consisting of methyl and ethyl;

$R^1$ and $R^2$ are preferably selected from the group consisting of methyl, ethyl, n-propyl, isopropyl, n-butyl, isobutyl, n-pentyl, n-hexyl, n-heptyl, n-octyl, butanedi-1,4-yl, pentanedi-1,5-yl, hexanedi-1,6-yl and phenyl.

$R^3$ and $R^4$ are preferably selected from the group consisting of H, $(C_6-C_{14})$-aryl, CN, COO—$(C_1-C_{18})$-alkyl, CONH—$(C_1-C_{18})$-alkyl and $CF_3$.

A ring is preferably formed between the radicals $R^1$ and $R^2$ or $R^1$ and $R^4$ or $R^3$ and $R^4$, where the ring preferably has in total 5, 6 or 7 ring atoms.

In the context of the present invention, the term ester imide refers to compounds of the general formula (III)

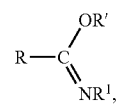

wherein

R' is selected from the group consisting of $(C_1-C_{24})$-alkyl, $(C_3-C_{20})$-cycloalkyl, $(C_2-C_{13})$-heterocycloalkyl;

R is selected from the group consisting of H, $(C_1-C_{24})$-alkyl, $(C_3-C_{20})$-cycloalkyl, $(C_2-C_{13})$-heterocycloalkyl, $(C_6-C_{14})$-aryl or $(C_3-C_{13})$-heteroaryl, CN, COO—$(C_1-C_{13})$-alkyl, CONH—$(C_1-C_{13})$-alkyl, $CF_3$;

$R^1$ is selected from the group consisting of H, $(C_1-C_{24})$-alkyl, $(C_3-C_{20})$-cycloalkyl, $(C_2-C_{13})$-heterocycloalkyl, $(C_6-C_{14})$-aryl or $(C_3-C_{13})$-heteroaryl;

where also from in each case two radicals selected from R, $R^1$ and R' together, a $(C_2-C_8)$-alkylene bridge can be formed, thus giving a ring with in total 4-11 ring atoms.

The term ester imide in the context of the present invention does not include the hydrochlorides of the ester imides.

R is preferably selected from the group consisting of H, methyl, ethyl, n-propyl, n-butyl, isobutyl, n-pentyl, n-hexyl, cyclohexyl, n-heptyl, n-octyl, phenyl, pyridyl, naphthyl.

R' is preferably selected from the group consisting of methyl, ethyl, and benzyl;

$R^1$ is preferably selected from the group consisting of hydrogen, methyl, ethyl, n-propyl, isopropyl, n-butyl, isobutyl, n-heptyl, n-hexyl, n-octyl, benzyl and phenyl.

A ring is preferably formed between the radicals R and $R^1$ or $R^1$ and R', where the ring preferably has in total 5, 6 or 7 ring atoms.

A $(C_1-C_n)$-alkyl radical is understood as meaning either linear or branched alkyl radicals having 1 to n carbon atoms. In the case of branched alkyl radicals, the branching can occur on any desired carbon atom. Preferred $(C_1-C_n)$-alkyl radicals are methyl, ethyl, n-propyl, isopropyl, n-butyl, isobutyl, sec-butyl, n-pentyl, isopentyl, n-hexyl, n-heptyl, n-octyl, n-nonyl, n-decyl, n-dodecyl and n-octadecyl.

The $(C_1-C_n)$-alkyl radical can be substituted or unsubstituted.

A $(C_3-C_n)$-cycloalkyl radical refers to a mono-, bi- or tricyclic, aliphatic system of in total 3 to n carbon atoms, where each ring can be three-, four-, five-, six- or seven-membered. Preference is given to $(C_6-C_{12})$-cycloalkyl radicals. Particularly preferred $(C_3-C_n)$-cycloalkyl radicals are cyclopropyl, cyclobutyl, cyclopentyl, cyclohexyl, cycloheptyl and 1-adamantyl, 9-fluorenyl.

The $(C_3-C_n)$-cycloalkyl radical can be substituted or unsubstituted.

A $(C_2-C_n)$-heterocycloalkyl radical refers to a mono-, bi- or tricyclic, aliphatic system of in total 2 to n carbon atoms, where each ring can be three-, four-, five-, six- or seven-membered, and where the number of heteroatoms, selected from the group N, O, and S, is 1 or 2 and the heteroatoms are identical or different. Preferred heterocycloalkyl radicals are 2-,3-tetrahydrofuryl, 1-,2-,3-pyrrolidinyl, 1-,2-,3-,4-piperidinyl, 1-,2-piperazinyl, 1-,2-,3-morpholinyl, tetrahydropyranyl-2 or -3 and 2,3-dihydrobenzothiophenyl-2 or -3.

The $(C_2-C_n)$-heterocycloalkyl radical can be substituted or unsubstituted.

A $(C_6-C_n)$-aryl radical refers to a mono-, bi- and tricyclic aromatic system with 6 to n carbon atoms, where each ring can in each case be five-, six- or seven-membered. Preferred $(C_6-C_n)$-aryl radicals are phenyl, naphthyl, anthryl, phenanthryl, biphenyl.

The $(C_6-C_n)$-aryl radical can be substituted or unsubstituted.

A $(C_3-C_n)$-heteroaryl radical refers to a mono-, bi- or tricyclic, aromatic system of in total 3 to n carbon atoms, where each ring can in each case be five-, six- or seven-membered, and where the number of heteroatoms, selected from the group N, O, and S, is 1 or 2 and the heteroatoms are identical or different. Preferred $(C_2-C_n)$-heteroaryl radicals are 2-, 3-furyl, 2-,3-pyrrolyl, 2-,4-,5-imidazolyl, 2-,3-thienyl, 2-,3-,4-pyridyl, 2-,3-,4-,5-,6-, 7-indolyl, 3-,4-,5-pyrazolyl, 2-,4-,5-,6-pyrimidinyl, acridinyl, quinolinyl, phenanthridinyl, benzothienyl. It can be substituted or unsubstituted.

Substituents are selected from the group consisting of halogens such as F, Cl, Br, I, and heteroatom-containing functional groups which contain one or more atoms selected from the group consisting of N, O, P, S, or Si, where single and multiple substitution is possible. Examples of heteroatom-containing functional groups are carbonyl, carboxyl, sulphonate, phosphonate, hydroxyl, silyl, amino, ammonium groups such as —OH,
—$(C_1-C_8)$-alkyloxy
—COOH,
—NH($\{C_1-C_8\}$-acyl),
—NH($\{C_1-C_8\}$-acyloxy)
—N($(C_1-C_{20})$-alkyl) ($\{C_1-C_8\}$-acyl),
—N($\{C_6-C_{14}\}$-aryl) ($\{C_1-C_8\}$-acyl),
—N($\{C_6-C_{14}\}$-aralkyl) ($\{C_1-C_8\}$-acyl),
—N($\{C_1-C_8\}$-acyl)$_2$,
—$NH_3^+$,
—NH($\{C_1-C_{20}\}$-alkyl)$_2^+$,
—NH($\{C_6-C_{14}\}$-aryl)$_2^+$,
—NH($\{C_6-C_{14}\}$-aralkyl)$_2^+$,
—NH($\{C_1-C_{20}\}$-alkyl) ($\{C_6-C_{14}\}$-aryl)$^+$,
—N($\{C_6-C_{14}\}$-aryl) ($\{C_1-C_{20}\}$-alkyl)$^+$,
—N($\{C_6-C_{14}\}$-aryl)$_2$($\{C_1-C_{20}\}$-alkyl)$^+$,
—O—C(=O)—O—$\{C_1-C_{20}\}$-alkyl,
—O—C(=O)—O—$\{C_6-C_{14}\}$-aryl,
—O—C(=O)—O—$\{C_6-C_{14}\}$-aralkyl,
—NH—C(=O)—O—$\{C_1-C_{20}\}$-alkyl,
—NH—C(=O)—O—$\{C_6-C_{14}\}$-aryl,
—NH—C(=O)—O—$\{C_6-C_{14}\}$-aralkyl,
—O—C(=O)—NH—$\{C_1-C_{20}\}$-alkyl,
—O—C(=O)—NH—$\{C_6-C_{14}\}$-aryl,
—O—C(=O)—NH—$\{C_6-C_{14}\}$-aralkyl,
—CN,
—$SO_2$—O—$\{C_1-C_{20}\}$-alkyl,
—$SO_2$—O—$\{C_6-C_{14}\}$-aryl,
—$SO_2$—O—$\{C_6-C_{14}\}$-aralkyl,
—$SO_2$—$\{C_1-C_{20}\}$-alkyl,
—$SO_2$—$\{C_6-C_{14}\}$-aryl,
—$SO_2$—$\{C_6-C_{14}\}$-aralkyl,
—SO—$\{C_1-C_{20}\}$-alkyl,
—SO—$\{C_6-C_{14}\}$-aryl,
—SO—$\{C_6-C_{14}\}$-aralkyl,
—Si($\{C_1-C_{20}\}$-alkyl)$_3$,
—Si($\{C_6-C_{14}\}$-aryl)$_3$,
—Si($\{C_6-C_{14}\}$-aryl) ($\{C_1-C_{20}\}$-alkyl)$_2$,
—Si($\{C_6-C_{14}\}$-aryl)$_2$($\{C_1-C_{20}\}$-alkyl),
$\{C_1-C_{20}\}$-perfluoroalkyl,
—PO(O—$\{C_1-C_{20}\}$-alkyl)$_2$,
—PO(O—$\{C_6-C_{14}\}$-aryl)$_2$,
—PO(O—$\{C_1-C_{20}\}$-alkyl) (O—$\{C_6-C_{14}\}$-aryl),
—PO($\{C_1-C_{20}\}$-alkyl)$_2$,
—PO($\{C_6-C_{14}\}$-aryl)$_2$,
—PO($\{C_1-C_{20}\}$-alkyl) ($\{C_6-C_{14}\}$-aryl).

In the context of the present invention, $(C_1-C_n)$-alkyloxy is defined as linear or branched $(C_1-C_n)$-alkyl group with 1 to n carbon atoms, with the proviso that this is bonded to the molecule carrying this group via an oxygen atom.

In the context of the present invention, $(C_1-C_n)$-acyl is defined as a group with the general structure R—(C=O)— with in total 1 to n carbon atoms, where R is selected from the group consisting of H, $(C_1-C_{n-1})$-alkyl, $(C_1-C_{n-1})$-alkenyl, $(C_6-C_{n-1})$-aryl, $(C_6-C_{n-1})$-heteroaryl and $(C_2-C_{n-1})$-alkynyl.

In the context of the present invention, $(C_1-C_n)$-acyloxy is a group with the general structure R'—(C=O)O— with in total 1 to n carbon atoms, where R' is selected from the group consisting of H, $(C_1-C_{n-1})$-alkyl, $(C_1-C_{n-1})$-alkenyl, $(C_6-C_{n-1})$-aryl, $(C_6-C_{n-1})$-heteroaryl and $(C_2-C_{n-1})$-alkynyl.

In the context of the present invention, $(C_2-C_n)$-alkenyl is defined as linear or branched $(C_2-C_n)$-alkyl group with 2 to n carbon atoms, with the proviso that this has a C—C double bond.

In the context of the present invention, $(C_2-C_n)$-alkynyl is defined as linear or branched $(C_2-C_n)$-alkyl group with 2 to n carbon atoms, with the proviso that this has a C—C triple bond.

In the context of the present invention, $(C_6-C_n)$-aralkyl refers to a group which contains both an alkyl and an aryl group and has in total 6 to n carbon atoms. The aralkyl group can be bonded to the molecule carrying this group via any of its carbon atoms. A $(C_6-C_n)$-aralkyl group can also be substituted with at least one substituent, where the substituents independently of one another are selected from the group consisting of halogen, $(C_1-C_8)$-alkyl, $(C_1-C_8)$-alkyloxy, —$NH_2$, —NO, —$NO_2$, $NH(C_1-C_8)$-alkyl, —$N((C_1-C_8)$-alkyl$)_2$, —OH, —$CF_3$, —$C_nF_{2n+1}$ (where n is an integer from 2 to 5), $NH(C_1-C_8)$-acyl, —$N((C_1-C_8)$-acyl$)_2$, $(C_1-C_8)$-acyl, $(C_1-C_8)$-acyloxy, —$SO_2$—$(C_1-C_8)$-alkyl, —$SO_2$—$(C_6-C_{14})$-aryl, —SO—$(C_1-C_8)$-alkyl, —SO—$(C_6-C_{14})$-aryl, —PO(O—$\{C_1-C_{20}\}$-alkyl$)_2$, —PO(O—$\{C_6-C_{14}\}$-aryl$)_2$, —PO(O—$\{C_1-C_{20}\}$-alkyl) (O—$\{C_6-C_{14}\}$-aryl), —PO($\{C_1-C_{20}\}$-alkyl$)_2$, —PO($\{C_6-C_{14}\}$-aryl$)_2$, —PO($\{C_1-C_{20}\}$-alkyl) ($\{C_6-C_{14}\}$-aryl).

As hydrogenation catalyst, it is possible to select all hydrogenation catalysts contemplated by the person skilled in the art for this purpose. Preference is given to using those hydrogenation catalysts which contain at least one active metal. Preferably, the active metal is one of groups VII B and/or VIII B of the Periodic Table of the Elements, with precious metals and Ni being preferred, and Ru, Rh, Pd, Pt, Re and Ni being particularly preferred. The metals can be present in the hydrogenation catalyst either (a) as such or in the form of oxides or (b) as metal complexes.

In case (a), the metal or metal oxide can either be applied to a support or be used as particles. The support material is not limited, usually customary supports such as aluminium oxide, silicon dioxide, iron oxide, magnesium oxide, zirconium dioxide, carbon or similar supports known to the person skilled in the art in the field of hydrogenation are used. The content of metal or metal oxide on the support is selected in a range of from 1% by weight to 25% by weight, based on the total weight of the catalyst. Preferably, a content of from 1 to 5% by weight of metal or metal oxide on the support is selected.

Examples of such hydrogenation catalysts are Pt/C, Pd/C, Rh/C, Ru/C, Pd/$CaCO_3$, Pd/$Al_2O_3$, Ru/$Al_2O_3$, Rh/$Al_2O_3$, Pd/Re/C, Pt/Re/C, $RuO_2$.

In case (b), the metals can also be used in the form of metal complexes as hydrogenation catalysts. Examples thereof are metal complexes of the metals Rh, Ir or Ru, such as e.g. the Wilkinson catalyst $ClRh(PPh_3)_3$ or [(dppb)Rh(cod)]$BF_4$, [Ir($PCy_3$ ($C_5H_5N$) (cod)]$PF_6$, [$Cl_2Ru(PPh_3)_3$] and [(dppb)Ru(metallyl)$_2$].

Preferably, the hydrogenation catalyst is selected from the group consisting of Pd/C, Pd/$Al_2O_3$, Pd/$CaCO_3$, Pt/C, Ru/$Al_2O_3$, Pd/Re/C, Pt/Re/C and [(dppb)Rh(cod)]$BF_4$. Particular preference is given to 5% Pd/C, 5% Pd/$Al_2O_3$, 5% Pd/$CaCO_3$, 5% Pt/C, 5% Ru/$Al_2O_3$, and [(dppb)Rh(cod)]$BF_4$.

The amount of hydrogenation catalyst can be freely selected by the person skilled in the art, where the molar ratio of hydrogenation catalyst to amide acetal or ketene N,O-acetal or ester imide is in a range of from 1:10 to 1:100 000. Further preference is given to a range of from 1:20 to 1:10 000, particular preference being given to a range of from 1:50 to 1:2000.

The hydrogen pressure of the reaction is established in a range of from 0.1 to 200 bar, preferably of from 0.1 to 100 bar, and particularly preferably of from 0.1 to 60 bar.

The temperature which is to be established during the reaction can be determined by the person skilled in the art and is usually in a range of from 0° C. to 250° C. It should be high enough that the envisaged reaction proceeds in a sufficiently rapid time but be as low as possible so that the byproduct spectrum during the reaction according to the invention can be kept as low as possible. Preferably, a temperature from the range of from 0° C. to 120° C. is established. Particularly preferably, a temperature from the range of from 10° C. to 100° C. is established, very particularly preferably a temperature from the range of from 20° C. to 50° C. is established.

In principle, the person skilled in the art is free to select the solvent that he would like to use in the process according to the invention. On account of the fact that the starting materials are often in liquid form, it is in this regard also possible to dispense with using a solvent. If, however, the use of solvents in the process according to the invention is desired, it is advantageous to use those solvents which accordingly readily dissolve the components of the reaction used and otherwise have proven to be inert towards the reaction according to the invention. Examples include polar or nonpolar solvents, in particular inter alia hydrocarbons, chlorinated hydrocarbons, ethers, esters and alcohols. Preference is given here to alkanes, haloalkanes, monohydric and polyhydric alcohols, cyclic and acyclic ethers, and esters.

Preferred solvents are those selected from the group consisting of hexane, heptane, octane, dimethyl glycol ether (DMGE), 1,4-dioxane, methyl tert-butyl ether (MTBE), tetradydrofuran (THF), ethyl acetate, isopropyl acetate, dibutyl ether, dimethyl carbonate, diethyl carbonate, dipropyl carbonate, methanol, ethanol, isopropanol, butanol, ethylene glycol, dichloromethane, 1,2-dichloroethane. Particular preference is given to methanol and ethanol.

It is advantageous to work under anhydrous conditions, such that preferably anhydrous solvent is used.

For the preparation of amide acetals, ketene N,O-acetals and ester imides, moreover, all reactions suitable for this purpose according to the person skilled in the art can be selected. Amide acetals can be generated e.g. by exchanging amines and acetals, whereas ester imides can be generated e.g. by alcoholysis of chloroimines.

A particular embodiment of the invention is a process for the preparation of amines, where the hydrogenation catalyst comprises at least one active metal.

A particular embodiment of the invention is a process for the preparation of amines, where the hydrogenation catalyst comprises at least one active metal of group VII B and/or VIII B of the Periodic Table of the Elements.

A particular embodiment of the invention is a process for the preparation of amines, where the reaction is carried out in a solvent.

A particular embodiment of the invention is a process for the preparation of amines, where the solvent is selected from the group consisting of hydrocarbons, chlorinated hydrocarbons, ethers, esters and alcohols.

A particular embodiment of the invention is a process for the preparation of amines, where anhydrous solvent is used.

A further particular embodiment of the invention is a process for the preparation of amines, where the reaction is carried out without solvents.

The invention further provides an amine obtainable by a process comprising the following steps:

a. Reaction of an
 i. amide acetal of the general formula (I),

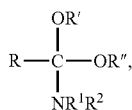

where
  R is selected from the group consisting of H, $(C_1\text{-}C_{24})$-alkyl, $(C_3\text{-}C_{20})$-cycloalkyl, $(C_2\text{-}C_{13})$-heterocycloalkyl, $(C_6\text{-}C_{14})$-aryl or $(C_3\text{-}C_{13})$-heteroaryl, CN, COO—$(C_1\text{-}C_{13})$-alkyl, CONH—$(C_1\text{-}C_{13})$-alkyl, $CF_3$;
  R' and R" independently of one another are selected from the group $(C_1\text{-}C_{24})$-alkyl, $(C_3\text{-}C_{20})$-cycloalkyl, $(C_2\text{-}C_{13})$-heterocycloalkyl;
  and
  $R^1$ and $R^2$ independently of one another are selected from the group consisting of H, $(C_1\text{-}C_{24})$-alkyl, $(C_3\text{-}C_8)$-cycloalkyl, $(C_2\text{-}C_7)$-heterocycloalkyl, $(C_6\text{-}C_{14})$-aryl and $(C_3\text{-}C_{13})$-heteroaryl;
  where also from in each case two radicals selected from R, $R^1$, $R^2$, R' and R" together, a $(C_2\text{-}C_8)$-alkylene bridge can be formed, thus giving a ring with in total 4-11 ring atoms;
 or
 ii. ketene N,O-acetal of the general formula (II),

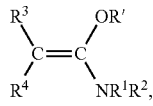

where
  R' is selected from the group consisting of $(C_1\text{-}C_{24})$-alkyl, $(C_3\text{-}C_{20})$-cycloalkyl, $(C_2\text{-}C_{13})$-heterocycloalkyl; and
  $R^1$, $R^2$ independently of one another are selected from the group consisting of H, $(C_1\text{-}C_{24})$-alkyl, $(C_3\text{-}C_{20})$-cycloalkyl, $(C_2\text{-}C_{13})$-heterocycloalkyl, $(C_6\text{-}C_{14})$-aryl and $(C_3\text{-}C_{13})$-heteroaryl;
  $R^3$ and $R^4$ independently of one another are selected from the group consisting of H, $(C_1\text{-}C_{24})$-alkyl, $(C_3\text{-}C_{20})$-cycloalkyl, $(C_2\text{-}C_{13})$-heterocycloalkyl, $(C_6\text{-}C_{14})$-aryl and $(C_3\text{-}C_{13})$-heteroaryl, CN, COO—$(C_1\text{-}C_{18})$-alkyl, CONH—$(C_1\text{-}C_{18})$-alkyl and $CF_3$,
  where also from in each case two radicals selected from $R^1$, $R^2$, $R^3$, $R^4$ and R' together, a $(C_2\text{-}C_8)$-alkylene bridge can be formed, thus giving a ring with in total 3-11 ring atoms;
 or
 iii. ester imide of the general formula (III)

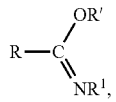

where
  R' is selected from the group consisting of $(C_1\text{-}C_{24})$-alkyl, $(C_3\text{-}C_{20})$-cycloalkyl, $(C_2\text{-}C_{13})$-heterocycloalkyl;

R is selected from the group consisting of H, $(C_1\text{-}C_{24})$-alkyl, $(C_3\text{-}C_{20})$-cycloalkyl, $(C_2\text{-}C_{13})$-heterocycloalkyl, $(C_6\text{-}C_{14})$-aryl or $(C_3\text{-}C_{13})$-heteroaryl, CN, COO—$(C_1\text{-}C_{18})$-alkyl, CONH—$(C_1\text{-}C_{18})$-alkyl, $CF_3$;
  $R^1$ is selected from the group consisting of H, $(C_1\text{-}C_{24})$-akyl, $(C_3\text{-}C_{20})$-cycloalkyl, $(C_2\text{-}C_{13})$-heterocycloalkyl, $(C_6\text{-}C_{14})$-aryl or $(C_3\text{-}C_{13})$-heteroaryl;
  where also from in each case two radicals selected from R, $R^1$ and R' together, a $(C_2\text{-}C_8)$-alkylene bridge can be formed, thus giving a ring with in total 4-11 ring atoms;
with $H_2$ in the presence of a hydrogenation catalyst, where catalyst and amide acetal or ketene N,O-acetal or ester imide are used in a molar ratio of from 1:10 to 1:100 000 and where a hydrogen pressure of from 0.1 bar to 200 bar is established and where a temperature in the range of from 0° C. to 250° C. is established.

Preferred reaction conditions during the hydrogenation can be found in Table 1.

TABLE 1

Preferred reaction conditions during the hydrogenation.

| Pressure | Temperature | Hydrogenation catalyst | Solvent | Molar ratio catalyst:starting material |
|---|---|---|---|---|
| 0.1-200 | 0° C.-250° C. | [a] | yes | 1:10-1:100 000 |
| 0.1-200 | 0° C.-250° C. | [a] | no | 1:10-1:100 000 |
| 0.1-200 | 0° C.-120° C. | [a] | yes | 1:10-1:100 000 |
| 0.1-200 | 0° C.-120° C. | [a] | no | 1:10-1:100 000 |
| 0.1-200 | 10° C.-100° C. | [a] | yes | 1:10-1:100 000 |
| 0.1-200 | 10° C.-100° C. | [a] | no | 1:10-1:100 000 |
| 0.1-100 | 0° C.-250° C. | [a] | yes | 1:10-1:100 000 |
| 0.1-100 | 0° C.-250° C. | [a] | no | 1:10-1:100 000 |
| 0.1-100 | 0° C.-120° C. | [a] | yes | 1:10-1:100 000 |
| 0.1-100 | 0° C.-120° C. | [a] | no | 1:10-1:100 000 |
| 0.1-100 | 10° C.-100° C. | [a] | yes | 1:10-1:100 000 |
| 0.1-100 | 10° C.-100° C. | [a] | no | 1:10-1:100 000 |
| 0.1-60 | 0° C.-250° C. | [a] | yes | 1:10-1:100 000 |
| 0.1-60 | 0° C.-250° C. | [a] | no | 1:10-1:100 000 |
| 0.1-60 | 0° C.-120° C. | [a] | yes | 1:10-1:100 000 |
| 0.1-60 | 0° C.-120° C. | [a] | no | 1:10-1:100 000 |
| 0.1-60 | 10° C.-100° C. | [a] | yes | 1:10-1:100 000 |
| 0.1-60 | 10° C.-100° C. | [a] | no | 1:10-1:100 000 |
| 40 bar $H_2$ | 20° C.-50° C. | [a] | yes | 1:10-1:100 000 |
| 40 bar $H_2$ | 20°-50° C. | [a] | no | 1:10-1:100 000 |
| 0.1-200 | 0° C.-250° C. | [b] | yes | 1:10-1:100 000 |
| 0.1-200 | 0° C.-250° C. | [b] | no | 1:10-1:100 000 |
| 0.1-200 | 0° C.-120° C. | [b] | yes | 1:10-1:100 000 |
| 0.1-200 | 0° C.-120° C. | [b] | no | 1:10-1:100 000 |
| 0.1-200 | 10° C.-100° C. | [b] | yes | 1:10-1:100 000 |
| 0.1-200 | 10° C.-100° C. | [b] | no | 1:10-1:100 000 |
| 0.1-100 | 0° C.-250° C. | [b] | yes | 1:10-1:100 000 |
| 0.1-100 | 0° C.-250° C. | [b] | no | 1:10-1:100 000 |
| 0.1-100 | 0° C.-120° C. | [b] | yes | 1:10-1:100 000 |
| 0.1-100 | 0° C.-120° C. | [b] | no | 1:10-1:100 000 |
| 0.1-100 | 10° C.-100° C. | [b] | yes | 1:10-1:100 000 |
| 0.1-100 | 10° C.-100° C. | [b] | no | 1:10-1:100 000 |
| 0.1-60 | 0° C.-250° C. | [b] | yes | 1:10-1:100 000 |
| 0.1-60 | 0° C.-250° C. | [b] | no | 1:10-1:100 000 |
| 0.1-60 | 0° C.-120° C. | [b] | yes | 1:10-1:100 000 |
| 0.1-60 | 0° C.-120° C. | [b] | no | 1:10-1:100 000 |
| 0.1-60 | 10° C.-100° C. | [b] | yes | 1:10-1:100 000 |
| 0.1-60 | 10° C.-100° C. | [b] | no | 1:10-1:100 000 |
| 40 bar $H_2$ | 20° C.-50° C. | [b] | yes | 1:10-1:100 000 |
| 40 bar $H_2$ | 20° C.-50° C. | [b] | no | 1:10-1:100 000 |
| 0.1-200 | 0° C.-250° C. | [c] | yes | 1:10-1:100 000 |
| 0.1-200 | 0° C.-250° C. | [c] | no | 1:10-1:100 000 |
| 0.1-200 | 0° C.-120° C. | [c] | yes | 1:10-1:100 000 |
| 0.1-200 | 0° C.-120° C. | [c] | no | 1:10-1:100 000 |
| 0.1-200 | 10° C.-100° C. | [c] | yes | 1:10-1:100 000 |
| 0.1-200 | 10° C.-100° C. | [c] | no | 1:10-1:100 000 |
| 0.1-100 | 0° C.-250° C. | [c] | yes | 1:10-1:100 000 |
| 0.1-100 | 0° C.-250° C. | [c] | no | 1:10-1:100 000 |

TABLE 1-continued

Preferred reaction conditions during the hydrogenation.

| Pressure | Temperature | Hydrogenation catalyst | Solvent | Molar ratio catalyst:starting material |
|---|---|---|---|---|
| 0.1-100 | 0° C.-120° C. | [c] | yes | 1:10-1:100 000 |
| 0.1-100 | 0° C.-120° C. | [c] | no | 1:10-1:100 000 |
| 0.1-100 | 10° C.-100° C. | [c] | yes | 1:10-1:100 000 |
| 0.1-100 | 10° C.-100° C. | [c] | no | 1:10-1:100 000 |
| 0.1-60 | 0° C.-250° C. | [c] | yes | 1:10-1:100 000 |
| 0.1-60 | 0° C.-250° C. | [c] | no | 1:10-1:100 000 |
| 0.1-60 | 0° C.-120° C. | [c] | yes | 1:10-1:100 000 |
| 0.1-60 | 0° C.-120° C. | [c] | no | 1:10-1:100 000 |
| 0.1-60 | 10° C.-100° C. | [c] | yes | 1:10-1:100 000 |
| 0.1-60 | 10° C.-100° C. | [c] | no | 1:10-1:100 000 |
| 40 bar $H_2$ | 20° C.-50° C. | [c] | yes | 1:10-1:100 000 |
| 40 bar $H_2$ | 20° C.-50° C. | [c] | no | 1:10-1:100 000 |
| 0.1-200 | 0° C.-250° C. | [a] | yes | 1:20-1:10 000 |
| 0.1-200 | 0° C.-250° C. | [a] | no | 1:20-1:10 000 |
| 0.1-200 | 0° C.-120° C. | [a] | yes | 1:20-1:10 000 |
| 0.1-200 | 0° C.-120° C. | [a] | no | 1:20-1:10 000 |
| 0.1-200 | 10° C.-100° C. | [a] | yes | 1:20-1:10 000 |
| 0.1-200 | 10° C.-100° C. | [a] | no | 1:20-1:10 000 |
| 0.1-100 | 0° C.-250° C. | [a] | yes | 1:20-1:10 000 |
| 0.1-100 | 0° C.-250° C. | [a] | no | 1:20-1:10 000 |
| 0.1-100 | 0° C.-120° C. | [a] | yes | 1:20-1:10 000 |
| 0.1-100 | 0° C.-120° C. | [a] | no | 1:20-1:10 000 |
| 0.1-100 | 10° C.-100° C. | [a] | yes | 1:20-1:10 000 |
| 0.1-100 | 10° C.-100° C. | [a] | no | 1:20-1:10 000 |
| 0.1-60 | 0° C.-250° C. | [a] | yes | 1:20-1:10 000 |
| 0.1-60 | 0° C.-250° C. | [a] | no | 1:20-1:10 000 |
| 0.1-60 | 0° C.-120° C. | [a] | yes | 1:20-1:10 000 |
| 0.1-60 | 0° C.-120° C. | [a] | no | 1:20-1:10 000 |
| 0.1-60 | 10° C.-100° C. | [a] | yes | 1:20-1:10 000 |
| 0.1-60 | 10° C.-100° C. | [a] | no | 1:20-1:10 000 |
| 40 bar $H_2$ | 20° C.-50° C. | [a] | yes | 1:20-1:10 000 |
| 40 bar $H_2$ | 20° C.-50° C. | [a] | no | 1:20-1:10 000 |
| 0.1-200 | 0° C.-250° C. | [b] | yes | 1:20-1:10 000 |
| 0.1-200 | 0° C.-250° C. | [b] | no | 1:20-1:10 000 |
| 0.1-200 | 0° C.-120° C. | [b] | yes | 1:20-1:10 000 |
| 0.1-200 | 0° C.-120° C. | [b] | no | 1:20-1:10 000 |
| 0.1-200 | 10° C.-100° C. | [b] | yes | 1:20-1:10 000 |
| 0.1-200 | 10° C.-100° C. | [b] | no | 1:20-1:10 000 |
| 0.1-100 | 0° C.-250° C. | [b] | yes | 1:20-1:10 000 |
| 0.1-100 | 0° C.-250° C. | [b] | no | 1:20-1:10 000 |
| 0.1-100 | 0° C.-120° C. | [b] | yes | 1:20-1:10 000 |
| 0.1-100 | 0° C.-120° C. | [b] | no | 1:20-1:10 000 |
| 0.1-100 | 10° C.-100° C. | [b] | yes | 1:20-1:10 000 |
| 0.1-100 | 10° C.-100° C. | [b] | no | 1:20-1:10 000 |
| 0.1-60 | 0° C.-250° C. | [b] | yes | 1:20-1:10 000 |
| 0.1-60 | 0° C.-250° C. | [b] | no | 1:20-1:10 000 |
| 0.1-60 | 0° C.-120° C. | [b] | yes | 1:20-1:10 000 |
| 0.1-60 | 0° C.-120° C. | [b] | no | 1:20-1:10 000 |
| 0.1-60 | 10° C.-100° C. | [b] | yes | 1:20-1:10 000 |
| 0.1-60 | 10° C.-100° C. | [b] | no | 1:20-1:10 000 |
| 40 bar $H_2$ | 20° C.-50° C. | [b] | yes | 1:20-1:10 000 |
| 40 bar $H_2$ | 20° C.-50° C. | [b] | no | 1:20-1:10 000 |
| 0.1-200 | 0° C.-250° C. | [c] | yes | 1:20-1:10 000 |
| 0.1-200 | 0° C.-250° C. | [c] | no | 1:20-1:10 000 |
| 0.1-200 | 0° C.-120° C. | [c] | yes | 1:20-1:10 000 |
| 0.1-200 | 0° C.-120° C. | [c] | no | 1:20-1:10 000 |
| 0.1-200 | 10° C.-100° C. | [c] | yes | 1:20-1:10 000 |
| 0.1-200 | 10° C.-100° C. | [c] | no | 1:20-1:10 000 |
| 0.1-100 | 0° C.-250° C. | [c] | yes | 1:20-1:10 000 |
| 0.1-100 | 0° C.-250° C. | [c] | no | 1:20-1:10 000 |
| 0.1-100 | 0° C.-120° C. | [c] | yes | 1:20-1:10 000 |
| 0.1-100 | 0° C.-120° C. | [c] | no | 1:20-1:10 000 |
| 0.1-100 | 10° C.-100° C. | [c] | yes | 1:20-1:10 000 |
| 0.1-100 | 10° C.-100° C. | [c] | no | 1:20-1:10 000 |
| 0.1-60 | 0° C.-250° C. | [c] | yes | 1:20-1:10 000 |
| 0.1-60 | 0° C.-250° C. | [c] | no | 1:20-1:10 000 |
| 0.1-60 | 0° C.-120° C. | [c] | yes | 1:20-1:10 000 |
| 0.1-60 | 0° C.-120° C. | [c] | no | 1:20-1:10 000 |
| 0.1-60 | 10° C.-100° C. | [c] | yes | 1:20-1:10 000 |
| 0.1-60 | 10° C.-100° C. | [c] | no | 1:20-1:10 000 |
| 40 bar $H_2$ | 20° C.-50° C. | [c] | yes | 1:20-1:10 000 |
| 40 bar $H_2$ | 20° C.-50° C. | [c] | no | 1:20-1:10 000 |
| 0.1-200 | 0° C.-250° C. | [a] | yes | 1:50-1:2000 |
| 0.1-200 | 0° C.-250° C. | [a] | no | 1:50-1:2000 |
| 0.1-200 | 0° C.-120° C. | [a] | yes | 1:50-1:2000 |
| 0.1-200 | 0° C.-120° C. | [a] | no | 1:50-1:2000 |
| 0.1-200 | 10° C.-100° C. | [a] | yes | 1:50-1:2000 |
| 0.1-200 | 10° C.-100° C. | [a] | no | 1:50-1:2000 |
| 0.1-100 | 0° C.-250° C. | [a] | yes | 1:50-1:2000 |
| 0.1-100 | 0° C.-250° C. | [a] | no | 1:50-1:2000 |
| 0.1-100 | 0° C.-120° C. | [a] | yes | 1:50-1:2000 |
| 0.1-100 | 0° C.-120° C. | [a] | no | 1:50-1:2000 |
| 0.1-100 | 10° C.-100° C. | [a] | yes | 1:50-1:2000 |
| 0.1-100 | 10° C.-100° C. | [a] | no | 1:50-1:2000 |
| 0.1-60 | 0° C.-250° C. | [a] | yes | 1:50-1:2000 |
| 0.1-60 | 0° C.-250° C. | [a] | no | 1:50-1:2000 |
| 0.1-60 | 0° C.-120° C. | [a] | yes | 1:50-1:2000 |
| 0.1-60 | 0° C.-120° C. | [a] | no | 1:50-1:2000 |
| 0.1-60 | 10° C.-100° C. | [a] | yes | 1:50-1:2000 |
| 0.1-60 | 10° C.-100° C. | [a] | no | 1:50-1:2000 |
| 40 bar $H_2$ | 20° C.-50° C. | [a] | yes | 1:50-1:2000 |
| 40 bar $H_2$ | 20°-50° C. | [a] | no | 1:50-1:2000 |
| 0.1-200 | 0° C.-250° C. | [b] | yes | 1:50-1:2000 |
| 0.1-200 | 0° C.-250° C. | [b] | no | 1:50-1:2000 |
| 0.1-200 | 0° C.-120° C. | [b] | yes | 1:50-1:2000 |
| 0.1-200 | 0° C.-120° C. | [b] | no | 1:50-1:2000 |
| 0.1-200 | 10° C.-100° C. | [b] | yes | 1:50-1:2000 |
| 0.1-200 | 10° C.-100° C. | [b] | no | 1:50-1:2000 |
| 0.1-100 | 0° C.-250° C. | [b] | yes | 1:50-1:2000 |
| 0.1-100 | 0° C.-250° C. | [b] | no | 1:50-1:2000 |
| 0.1-100 | 0° C.-120° C. | [b] | yes | 1:50-1:2000 |
| 0.1-100 | 0° C.-120° C. | [b] | no | 1:50-1:2000 |
| 0.1-100 | 10° C.-100° C. | [b] | yes | 1:50-1:2000 |
| 0.1-100 | 10° C.-100° C. | [b] | no | 1:50-1:2000 |
| 0.1-60 | 0° C.-250° C. | [b] | yes | 1:50-1:2000 |
| 0.1-60 | 0° C.-250° C. | [b] | no | 1:50-1:2000 |
| 0.1-60 | 0° C.-120° C. | [b] | yes | 1:50-1:2000 |
| 0.1-60 | 0° C.-120° C. | [b] | no | 1:50-1:2000 |
| 0.1-60 | 10° C.-100° C. | [b] | yes | 1:50-1:2000 |
| 0.1-60 | 10° C.-100° C. | [b] | no | 1:50-1:2000 |
| 40 bar $H_2$ | 20° C.-50° C. | [b] | yes | 1:50-1:2000 |
| 40 bar $H_2$ | 20°-50° C. | [b] | no | 1:50-1:2000 |
| 0.1-200 | 0° C.-250° C. | [c] | yes | 1:50-1:2000 |
| 0.1-200 | 0° C.-250° C. | [c] | no | 1:50-1:2000 |
| 0.1-200 | 0° C.-120° C. | [c] | yes | 1:50-1:2000 |
| 0.1-200 | 0° C.-120° C. | [c] | no | 1:50-1:2000 |
| 0.1-200 | 10° C.-100° C. | [c] | yes | 1:50-1:2000 |
| 0.1-200 | 10° C.-100° C. | [c] | no | 1:50-1:2000 |
| 0.1-100 | 0° C.-250° C. | [c] | yes | 1:50-1:2000 |
| 0.1-100 | 0° C.-250° C. | [c] | no | 1:50-1:2000 |
| 0.1-100 | 0° C.-120° C. | [c] | yes | 1:50-1:2000 |
| 0.1-100 | 0° C.-120° C. | [c] | no | 1:50-1:2000 |
| 0.1-100 | 10° C.-100° C. | [c] | yes | 1:50-1:2000 |
| 0.1-100 | 10° C.-100° C. | [c] | no | 1:50-1:2000 |
| 0.1-60 | 0° C.-250° C. | [c] | yes | 1:50-1:2000 |
| 0.1-60 | 0° C.-250° C. | [c] | no | 1:50-1:2000 |
| 0.1-60 | 0° C.-120° C. | [c] | yes | 1:50-1:2000 |
| 0.1-60 | 0° C.-120° C. | [c] | no | 1:50-1:2000 |
| 0.1-60 | 10° C.-100° C. | [c] | yes | 1:50-1:2000 |
| 0.1-60 | 10° C.-100° C. | [c] | no | 1:50-1:2000 |
| 40 bar $H_2$ | 20° C.-50° C. | [c] | yes | 1:50-1:2000 |
| 40 bar $H_2$ | 20°-50° C. | [c] | no | 1:50-1:2000 |

[a] = Hydrogenation catalyst with at least one active metal of group VII B and/or VIII B of the Periodic Table of the Elements
[b] = Pd/C, Pd/Al$_2$O$_3$, Pd/CaCO$_3$, Pt/C, Ru/Al$_2$O$_3$, Pd/Re/C, Pt/Re/C or [(dppb)Rh(cod)]BF$_4$
[c] = 5% Pd/C, 5% Pd/Al$_2$O$_3$, 5% Pd/CaCO$_3$, 5% Pt/C, 5% Ru/Al$_2$O$_3$ or [(dppb)Rh(cod)]BF$_4$ In the process according to the invention, the procedure generally involves mixing, in an autoclave, the amide acetal or ester imide or ketene N,O-acetal and the hydrogenation catalyst in the stated molar ratio with a suitable amount of solvent. The autoclave is then flushed several times with hydrogen and the mixture is hydrogenated at a suitable pressure. After the hydrogen pressure has been let down, the reaction mixture is filtered off and the filtrate is worked up by processes known to the person skilled in the art.

WORKING EXAMPLES

The examples below serve to illustrate the invention without limiting it thereto.

Example 1

Reworking of Experiment 1 from the Patent Specification DE-604277 (1934)

In a 300 ml autoclave, benzyliminoethyl ether hydrochloride (37 g, 0.2 mol) is suspended in 30 ml of cooled absolute ethanol and, after adding 0.5 g of platinum oxide (Adams) catalyst, is flushed with hydrogen, then 40 bar hydrogen were injected in and the mixture was stirred at 30° C. and a constant pressure for 12 hours. After filtering from the catalyst and distilling off the solvent, the residue was admixed with 50 ml of 2N sodium hydroxide solution, and the product is extracted with diethyl ether. The organic phase is dried over $K_2CO_3$, the solvent is removed on a rotary evaporator, and the residue is analyzed by means of GC-MS and NMR spectroscopy. The mixture consists of 2% benzylamine, 21% (cyclohexylmethyl)amine and 77% di(cyclohexylmethyl)amine.

Examples 2-19

In a 10 ml autoclave, an amide acetal (5 mmol) is dissolved in 5 ml of absolute methanol, and, after adding 1 mol % catalyst, flushing with hydrogen is carried out. 40 bar of hydrogen are then injected in, and the mixture is stirred at 25° C. and a constant pressure until hydrogen absorption is no longer evident (1-2 h). After filtering off from the catalyst, the reaction solution is admixed with 10 ml of 1 M HCl solution in methanol, the solvent is removed on a rotary evaporator, and the residue is admixed with ether. The solid amine hydrochloride is filtered off, washed with diethyl ether and dried in vacuo.

Example 20-25

In an autoclave, 2-ethoxy-2-methyl-3-benzyloxazolidine (5.55 g, 25 mmol) is dissolved in 25 ml of absolute ethanol and, after adding 1 mol % catalyst, flushing with hydrogen is carried out. 40 bar of hydrogen are then injected in, and the mixture is stirred at 25° C. and a constant pressure until hydrogen absorption is no longer evident (2-3 h).

Separation off from the catalyst and distillation gives N-benzyl-2-(ethylamino)ethanol: b.p. 63° C./0.03 mbar; Rf=0.33 in ethyl acetate; $^1$H NMR (CDCl$_3$) δ 7.33-7.37 (m, 4H), 7.27-7.30 (m, 1H), 3.66 (s, 2H), 3.60 (t, J=5.4, 2H), 2.96 (br. s, OH), 2.69 (t, J=5.4, 2H), 2.61 (q, J=7.2, 2H), 1.10 (t, J=7.2, 3H).

The catalysts used and yields of Examples 2-25 can be found in Table 2.

TABLE 2

| | Yields of Examples 2-25. | | | |
|---|---|---|---|---|
| Examples | 2-7 | 8-13 | 14-19 | 20-25 |
| Amide acetal | MeO, OMe, H, NMe$_2$ | MeO, OMe, Me, NMe$_2$ | (cyclopentyl with OMe, OMe, NMe) | BnN, Me, EtO, O (oxazolidine) |
| Amine | NMe$_3$ | EtNMe$_2$ | (cyclopentyl NMe) | Et-N(Bn)-CH$_2$CH$_2$-OH |
| 5% Pd/C | 60% | 84% | 74% | 80% |
| 5% Pd/Al$_2$O$_3$ | 70% | 99% | 64% | 50% |
| 5% Pd/CaCO$_3$ | 74% | 93% | 69% | 40% |
| 5% Pt/C | 78% | 82% | 99% | 82% |
| 5% Ru/Al$_2$O$_3$ | 83% | 80% | 76% | 22% |
| [(dppb)Rh(cod)]BF$_4$ | 96% | 97% | 95% | 97% |

Examples 26-31

In an autoclave, an ester imide (25 mmol) is dissolved in 25 ml of absolute methanol or ethanol and, after adding 5% Pt/C (975 mg, 1 mol %), flushing with hydrogen is carried out. 40 bar of hydrogen are then injected in, and the mixture is stirred at 25° C. and constant pressure for 16 hours. After separation off from the catalyst, the filtrate is distilled.

The reaction conditions and yields can be found in Table 3.

TABLE 3

Reaction conditions and yields of Examples 26-31.

| Example | Ester imide | Product | Solvent | Yield, % |
|---|---|---|---|---|
| 26 | OEt, NPh (ethyl propanimidate, N-Ph) | NHPh propyl | EtOH | 86 |
| 27 | (tetrahydropyridine with OMe) | piperidine (NH) | MeOH | 84 |

TABLE 3-continued

Reaction conditions and yields of Examples 26-31.

| Example | Ester imide | Product | Solvent | Yield, % |
|---|---|---|---|---|
| 28 | 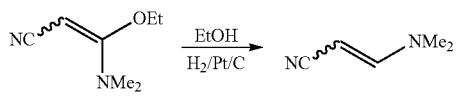 | | MeOH | 85 |
| 29 | | HO~~NHEt | — | 60 |
| | | HO~~NEt$_2$ | — | 19 |
| 30 | | $(C_5H_{11})_2NH$ | EtOH | 88 |
| 31 | | $Bn_2NH$ | EtOH | 85 |

Example 32

In an autoclave, 2-dimethylamino-2-ethoxy-1-cyanoethylene (7 g, 50 mmol) is dissolved in 20 ml of absolute ethanol. After adding 5% Pt/C (975 mg, 0.5 mol %), the autoclave is flushed with hydrogen, then 40 bar of hydrogen are injected in, and the mixture is stirred at 50° C. and a constant pressure for 16 hours. After filtering off from the catalyst and distilling off the solvent, the residue is taken up in diethyl ether, washed with concentrated NaCl solution and dried over MgSO$_4$. Distillation gives 3.1 g (65%) of 3-(dimethylamino)acrylonitrile; Kp=66° C./0.1 mbar, $^1$H NMR (CD$_2$Cl$_2$) (preferred isomer) δ 6.95 (d, J=13.6, 1H), 3.70 (d, J=13.5, 1H), 2.86 (br. S, 6H).

The invention claimed is:

1. A process for the preparation of amines, comprising reacting one or more compounds with H$_2$ in the presence of a hydrogenation catalyst, wherein said compounds are selected from the group consisting of:

a) an amide acetal of the general formula (I):

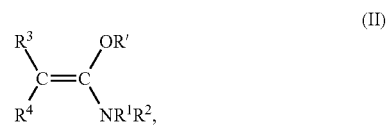

wherein:
R is selected from the group consisting of H, $(C_1$-$C_{24})$-alkyl, $(C_3$-$C_{20})$-cycloalkyl, $(C_2$-$C_{13})$-heterocycloalkyl, $(C_6$-$C_{14})$-aryl or $(C_3$-$C_{13})$-heteroaryl, CN, COO—$(C_1$-$C_{18})$-alkyl, CONH—$(C_1$-$C_{18})$-alkyl, CF$_3$;

R' and R" independently of one another are selected from the group consisting of: $(C_1$-$C_{24})$-alkyl, $(C_3$-$C_{20})$-cycloalkyl, and $(C_2$-$C_{13})$-heterocycloalkyl; and R$^1$ and R$^2$ independently of one another are selected from the group consisting of: H, $(C_1$-$C_{24})$-alkyl, $(C_3$-$C_8)$-cycloalkyl, $(C_2$-$C_7)$-heterocycloalkyl, $(C_6$-$C_{14})$-aryl and $(C_3$-$C_{13})$-heteroaryl;

and wherein, in each case, two radicals selected from R, R$^1$, R$^2$, R' and R" together can form a $(C_2$-$C_8)$-alkylene bridge, thus giving a ring with a total of 4-11 ring atoms;

b) a ketene N,O-acetal of the general formula (II):

wherein:
R' is selected from the group consisting of: $(C_1$-$C_{24})$-alkyl, $(C_3$-$C_{20})$-cycloalkyl, $(C_2$-$C_{13})$-heterocycloalkyl;

R$^1$, R$^2$, independently of one another, are selected from the group consisting of: H, $(C_1$-$C_{24})$-alkyl, $(C_3$-$C_{20})$-cycloalkyl, $(C_2$-$C_{13})$-heterocycloalkyl, $(C_6$-$C_{14})$-aryl and $(C_3$-$C_{13})$-heteroaryl;

R$^3$ and R$^4$, independently of one another, are selected from the group consisting of: H, $(C_1$-$C_{24})$-alkyl, $(C_3$-$C_{20})$-cycloalkyl, $(C_2$-$C_{13})$-heterocycloalkyl, $(C_6$-$C_{14})$-aryl, $(C_3$-$C_{13})$-heteroaryl, CN, COO—$(C_1$-$C_{18})$-alkyl, CONH—$(C_1$-$C_{18})$-alkyl and CF$_3$;

and wherein, in each case, two radicals selected from R$^1$, R$^2$, R$^3$, R$^4$ and R' together can form a $(C_2$-$C_8)$-alkylene bridge, thus giving a ring with a total of 3-11 ring atoms; and c) an ester imide of the general formula (III):

$$R-\underset{NR^1}{\overset{OR'}{C}} \quad (III)$$

wherein:
R' is selected from the group consisting of: $(C_1$-$C_{24})$-alkyl, $(C_3$-$C_{20})$-cycloalkyl, $(C_2$-$C_{13})$-heterocycloalkyl;

R is selected from the group consisting of: H, $(C_1$-$C_{24})$-alkyl, $(C_3$-$C_{20})$-cycloalkyl, $(C_2$-$C_{13})$-heterocycloalkyl, $(C_6$-$C_{14})$-aryl, $(C_3$-$C_{13})$-heteroaryl, CN, COO—$(C_1$-$C_{18})$-alkyl, CONH—$(C_1$-$C_{18})$-alkyl, and CF$_3$;

R$^1$ is selected from the group consisting of: H, $(C_1$-$C_{24})$-alkyl, $(C_3$-$C_{20})$-cycloalkyl, $(C_2$-$C_{13})$-heterocycloalkyl, $(C_6$-$C_{14})$-aryl and $(C_3$-$C_{13})$-heteroaryl;

and wherein, in each case, two radicals selected from R, R$^1$ and R' together can form a $(C_2$-$C_8)$-alkylene bridge, thus giving a ring with a total of 4-11 ring atoms;

and wherein said catalyst and said amide acetal, ketene N,O-acetal, or ester imide are used in a molar ratio of from 1:10 to 1:100 000 and the reaction is carried out at a hydrogen pressure of from 0.1 bar to 200 bar and a temperature of from 0° C. to 250° C.

2. The process of claim 1, wherein the hydrogenation catalyst comprises at least one active metal.

3. The process of claim 2, wherein the active metal is a metal of group VII B and/or VIII B of the Periodic Table of the Elements.

4. The process of claim 1, wherein the reaction is carried out in a solvent.

5. The process of claim 4, wherein the solvent is selected from the group consisting of hydrocarbons, chlorinated hydrocarbons, ethers, esters and alcohols.

6. The process of claim 5, wherein an anhydrous solvent is used.

7. The process of claim 1, wherein the reaction is carried out without solvents.

8. The process of claim 2, wherein the reaction is carried out in a solvent.

9. The process of claim 8, wherein the solvent is selected from the group consisting of hydrocarbons, chlorinated hydrocarbons, ethers, esters and alcohols.

10. The process of claim 9, wherein an anhydrous solvent is used.

11. The process of claim 2, wherein the reaction is carried out without solvents.

12. The process of claim 11, wherein the active metal is a metal of group VII B and/or VIII B of the Periodic Table of the Elements.

13. The process of claim 1, wherein the compounds comprise an amide acetal of formula (I) as described in paragraph a).

14. The process of claim 13, wherein the reaction is carried out in a solvent selected from the group consisting of hydrocarbons, chlorinated hydrocarbons, ethers, esters and alcohols.

15. The process of claim 13, wherein the reaction is carried out without solvents.

16. The process of claim 1, wherein the compounds comprise a ketene N,O-acetal of formula (II) as described in paragraph b).

17. The process of claim 16, wherein the reaction is carried out in a solvent selected from the group consisting of hydrocarbons, chlorinated hydrocarbons, ethers, esters and alcohols.

18. The process of claim 16, wherein the reaction is carried out without solvents.

19. The process of claim 1, wherein the compounds comprise an ester imide of formula (III) as described in paragraph c).

20. The process of claim 19, wherein the reaction is carried out without solvents.

* * * * *